(12) United States Patent
Goedeke et al.

(10) Patent No.: US 8,219,199 B2
(45) Date of Patent: Jul. 10, 2012

(54) SYSTEM AND METHOD FOR PROTECTING IMPLANTED MEDICAL DEVICES FROM INTERFERING RADIATED FIELDS

(75) Inventors: Steven D. Goedeke, Forest Lake, MN (US); Michael E. Nowak, Andover, MN (US); Christopher Stancer, Presscott, WI (US)

(73) Assignee: Medtronic, Inc., Minneapolis, MN (US)

( * ) Notice: Subject to any disclaimer, the term of this patent is extended or adjusted under 35 U.S.C. 154(b) by 508 days.

(21) Appl. No.: 12/388,926

(22) Filed: Feb. 19, 2009

(65) Prior Publication Data
US 2010/0211129 A1 Aug. 19, 2010

(51) Int. Cl.
*A61N 1/08* (2006.01)
(52) U.S. Cl. .......................................... 607/36
(58) Field of Classification Search .................. 607/36, 607/37, 45, 63, 115, 116, 119
See application file for complete search history.

(56) References Cited

U.S. PATENT DOCUMENTS

| | | | |
|---|---|---|---|
| 4,091,818 A | 5/1978 | Brownlee et al. | |
| 4,934,366 A | 6/1990 | Truex et al. | |
| 5,197,468 A | 3/1993 | Proctor et al. | |
| 5,683,434 A * | 11/1997 | Archer | 607/36 |
| 2008/0033497 A1* | 2/2008 | Bulkes et al. | 607/9 |
| 2009/0149933 A1* | 6/2009 | Ameri | 607/119 |

* cited by examiner

*Primary Examiner* — Niketa Patel
*Assistant Examiner* — Hiba El-Kaissi
(74) *Attorney, Agent, or Firm* — Stephen W. Bauer; Michael J. Ostrom

(57) ABSTRACT

An implantable medical device (IMD) can include an implantable pulse generator (IPG), such as a cardiac pacemaker or an implantable cardioverter-defibrillator (ICD). At least one lead is coupled to the IMD at a proximal end to the anatomic tissue of a patient at a distal end. According to various embodiments, a one-quarter wavelength open circuit terminated transmission line forms a stub filter to attenuate an interfering signal, such as those created by an MRI scanner during an MRI procedure. By cancelling the interfering signal, both the IMD and patient are protected from any adverse effects caused by the interfering signal.

15 Claims, 4 Drawing Sheets

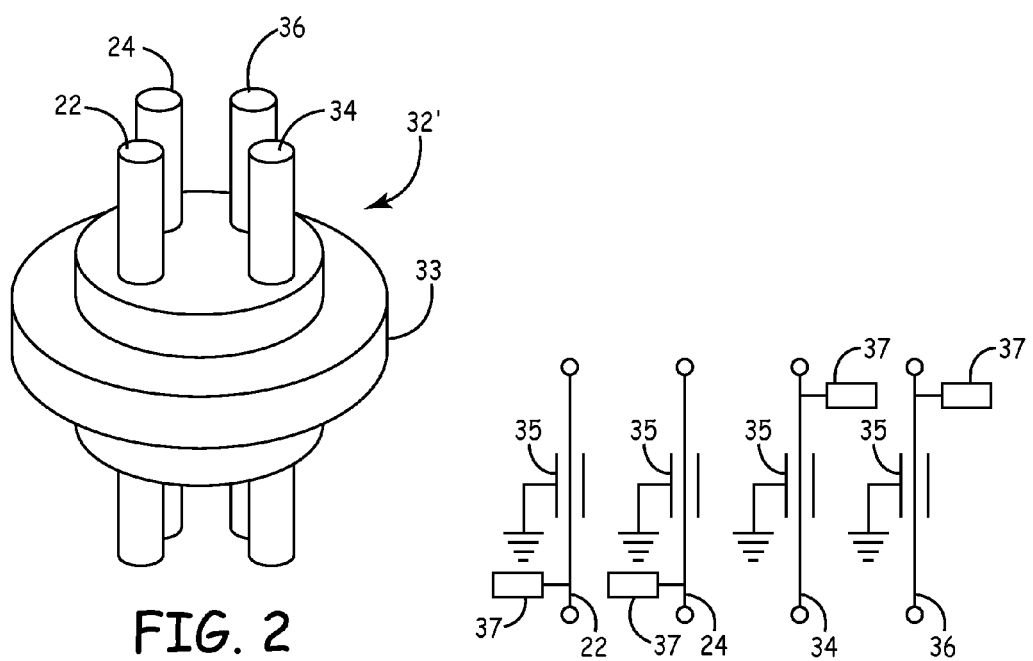

SYSTEM AND METHOD FOR PROTECTING IMPLANTED MEDICAL DEVICES FROM INTERFERING RADIATED FIELDS

FIELD

The present disclosure relates to implantable medical devices (IMDs), in particular to a system and method for use of quarter wavelength stub filter to protect IMDs from interfering radiated fields.

BACKGROUND

The statements in this section merely provide background information related to the present disclosure and may not constitute prior art.

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with implantable medical devices (IMDs). These devices can include implantable pulse generator (IPG) devices, pacemakers, implantable cardioverter-defibrillator (ICD) devices, cardiac resynchronization therapy defibrillator devices, implantable monitoring or diagnostic devices, neurostimulators or combinations thereof.

The IMD may include a lead that is directly connected to tissue to be affected by the IMD. The lead can include a tip portion that is directly connected to the anatomical tissue, such as a muscle bundle, and a lead body that connects to the device body or therapeutic driving device. It is generally known that the device body or case portion can be implanted in a selected portion of the anatomical structure, such as in a chest or abdominal wall, and the lead can be inserted through various venous portions so that the tip portion can be positioned at the selected position near or in the muscle group.

The IMD generally remains with the patient during the rest of the patient's natural life. To that end, the IMD can be exposed to various environmental factors. For example, the patient may undergo a magnetic resonance imaging (MRI) procedure or other high frequency imaging procedures. Magnetic resonance imaging has been developed as an imaging technique adapted to obtain both images of anatomical features of human patients as well as some aspects of the functional activities of biological tissue. These images have medical diagnostic value in determining the state of the health of the anatomical tissue examined.

In a magnetic-resonance imaging process, a patient is typically aligned to place the portion of the patient's anatomy to be examined in the imaging volume of the magnetic-resonance imaging apparatus. Such a magnetic-resonance imaging apparatus typically comprises a primary magnet for supplying a constant magnetic field which, by convention, is along the z-axis and is substantially homogeneous over the imaging volume and secondary magnets that can provide linear magnetic field gradients along each of three principal Cartesian axes in space. A magnetic field gradient refers to the variation of the field with respect to each of the three principal Cartesian axes.

The use of the magnetic-resonance imaging process with patients who have implanted medical devices, such as cardiac assist devices, often presents problems. As is known to those skilled in the art, implantable devices (such as implantable pulse generators and cardioverter/defibrillator/pacemakers) are sensitive to a variety of forms of electromagnetic interference because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures since one or more leads of the IMD may act as an antenna and have current or energy induced therein due to the MRI procedure. This induced current or energy can damage the IMD or anatomical tissue and cause injury to the patient. Accordingly, reduction or dissipation of the induced current or energy would be useful and beneficial to patients having an implanted medical device.

SUMMARY

An implantable medical device (IMD) can include implantable pulse generator (IPG) devices, implantable cardioverter-defibrillators (ICD), cardiac resynchronization therapy defibrillator devices, neurostimulators or combinations thereof. The IMD can be positioned in a selected portion of the anatomical structure, such as a chest wall or abdominal wall, and a lead can be positioned through a vein or transvenously so that a lead tip can be implanted in a portion of the cardiac or heart muscle. Various portions of the IMD, such as a case or device body, can be augmented according to this disclosure to include a one-quarter wavelength stub filter to reduce or eliminate detrimental affects to the IMD or the patient due to various external environmental factors.

According to the present invention, an implantable medical device is operable to sense signals from a patient or to provide a therapy to anatomical tissue of the patient in the presence of an interfering signal. The implanted medical device includes at least one lead coupled at a proximal end to the implanted medical device and coupled at a distal end to the anatomical tissue and has a conductor therein coupled to circuitry within the implanted medical device. An open circuit terminated transmission line having an electrical length approximately equal to one-quarter of a wavelength of the interfering signal is coupled to the conductor at the proximal end of the lead which causes a phase-shifted version of the interfering signal to be reflected through the open circuit terminated transmission line to attenuate the interfering signal.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 2 is an illustration of a feedthrough suitable for use with the techniques of this disclosure;

FIG. 3 is an equivalent electrical diagram of the feedthrough of FIG. 2;

DETAILED DESCRIPTION

Figure 1:
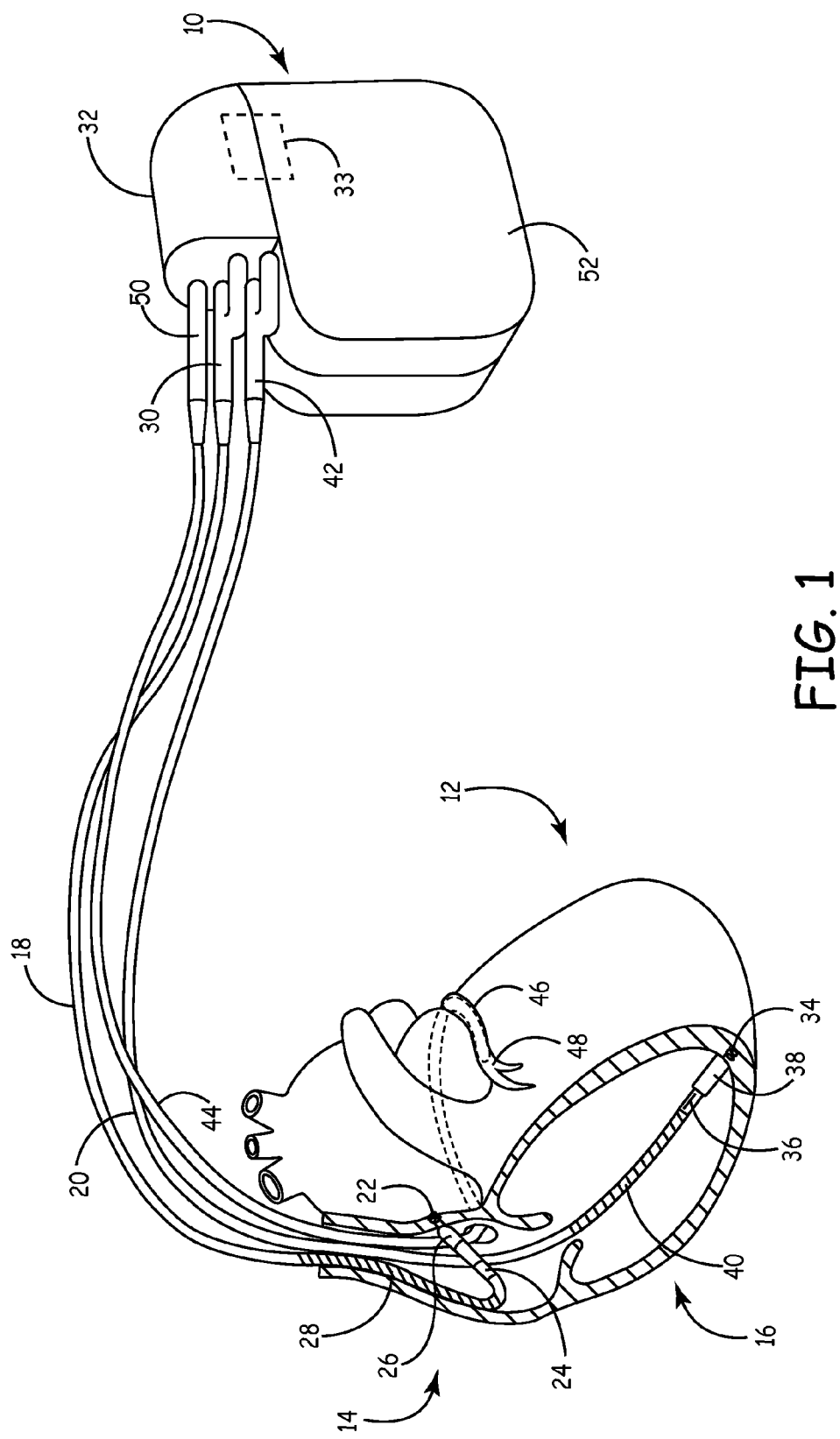
FIG. 1 is an illustration of an IMD coupled to a human heart.

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for use of a one-quarter wavelength open circuit terminated transmission line to reflect a phase-shifted waveform to create a standing wave to attenuate or cancel an interfering radiating field. The interfering radiating field may, for example, be a radiating field generated by an MRI scanner. The techniques of this disclosure may, however, be used to reduce or eliminate the effect of other interfering radiating fields, such as interfering radiating fields generated by any medical or non-medical device.

In this application, the one-quarter wavelength open circuit terminated transmission line becomes a stub filter to protect the internal circuitry of the IMD and/or the patient by reducing or eliminating detrimental affects to the IMD or the patient due to the interfering radiating field. For example, interfering radiating field may produce may induce energy on one or more implantable leads coupled to the IMD. In some instances, the IMD inappropriately detects the induced energy on the leads as physiological signals, which may in turn cause the IMD to deliver undesired therapy or withhold desired therapy. This inappropriate detection is sometimes referred to as oversensing. In other instances, the induced energy on the leads result in the IMD not detecting physiological signals that are actually present, which may again result in the IMD delivering undesired therapy or withholding desired therapy. It should be noted, however, that the present teachings could be applicable to any appropriate procedure in which it is desirable to have a component that is responsive to external fields.

Further, as used herein, the term module refers to an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. Therefore, it will be understood that the following discussions are not intended to limit the scope of the appended claims.

FIG. 1 depicts an exemplary implantable medical device (IMD) 10 that may practice the techniques of this disclosure. In the example of FIG. 1, IMD 10 is an implantable multi-chamber pacemaker that includes cardioversion and defibrillation capability. In one preferred embodiment, techniques of this disclosure may be practiced by a device that paces a single cardiac chamber or several chambers, that paces one or more atria or one or more ventricles, and that paces in any of several pacing modes. However, the techniques of this disclosure is not limited to the particular IMD shown in FIG. 1, however, but may be practiced by any number of implantable devices, such as devices that provide stimulation therapy to other locations in the patient, including a stomach, brain, spinal cord, pelvic floor or other location in the patient. Moreover, the techniques of this disclosure are not limited to therapy delivery devices, but may also be practiced in monitoring or diagnostic devices, or devices that provide combinations of therapy, monitoring and diagnostics.

In one exemplary embodiment, IMD 10 includes an implantable pulse generator (IPG) (not shown in FIG. 1) that generates pacing stimuli to administer one or more pacing therapies to heart 12. Pacing stimuli may be applied to the right atrium 14, for example, or the right ventricle 16, or both. IMD 10 also includes circuitry to sense atrial and ventricular activations. In some instances, atrial and ventricular bipolar pace/sense electrode pairs at the distal ends of leads 18 and 20, respectively, carry out the pacing and sensing functions. In other instances, the pacing and sensing functions may be performed as unipolar, e.g., using one the electrodes located on the distal end of the respective lead and the housing or can of IMD 10 as the return electrode.

In right atrium 14, the distal end of atrial lead 18 includes an extendable helical, pace/sense tip electrode 22 and a pace/sense ring electrode 24. Helical electrode 22 extends from electrode head 26 into the atrial appendage. Pace/sense electrodes 22 and 24 are employed for atrial pacing and for sensing of P-waves indicative of atrial activation. The distal end of atrial lead 18 also includes an elongated coil defibrillation electrode 28 that can deliver a defibrillation shock to right atrium 14. Electrode 28 may also be used to deliver cardioversion therapy to right atrium 14.

Atrial lead 18 may include conductors that electrically couple electrodes 22, 24 and 28 to IMD 10. The conductors may be arranged coaxially, coradially, in parallel, or in another configuration, and may be insulated from one another and from the tissue of the patient. The proximal end of atrial lead 18 may include a bifurcated connector 30 that couples the conductors to a connector block 32 on IMD 10 and the conductors couple to internal circuitry via feedthrough 33.

In right ventricle 16, the distal end of ventricular lead 20 likewise may include a pace/sense tip electrode 34 and a pace/sense ring electrode 36. Pace/sense tip electrode 34 may be a helical electrode that extends from electrode head 38 toward the apex of heart 12. Pace/sense electrodes 34 and 36 are employed for ventricular pacing and for sensing of R-waves indicative of ventricular activation. The distal end of ventricular lead 20 also includes an elongated coil defibrillation electrode 40 that can deliver a defibrillation shock or cardioversion therapy to right ventricle 16.

Like atrial lead 18, ventricular lead 20 may include one or more insulated conductors that electrically couple electrodes 34, 36 and 40 to IMD 10. The proximal end of ventricular lead 20 may include a bifurcated connector 42 that couples the conductors to connector block 32 and the conductors couple to internal circuitry via feedthrough 33.

FIG. 1 also illustrates deployment of a coronary sinus lead 44. Coronary sinus lead 44 may include one or more insulated conductors. The proximal end of coronary sinus lead 44 may include one or more electrodes, such as pace/sense electrode 46. Pace/sense electrode 46 may be deployed within the great vein 48 of heart 12, and may be used to deliver pacing therapies to the left side of heart 12. A connector 50 at the proximal end of the coronary sinus lead 44 couples the conductors in lead 44 to connector block 32 and the conductors couple to internal circuitry via feedthrough 33. In some embodiments, coronary sinus lead 44 may include an elongated exposed coil wire defibrillation electrode (not shown).

IMD 10 includes a housing 52 that may serve as a "can" electrode. In unipolar pacing operations, IMD 10 may deliver an electrical stimulation to heart 12 via an electrode disposed on one or more of leads 18, 20 or 44, with housing 52 being a part of the return current path. In bipolar pacing operation, by contrast, IMD 10 may deliver an electrical stimulation to heart 12 via a tip electrode, with a ring electrode providing the principal return current path. IMD 10 may also perform unipolar sensing using the using an electrode disposed on one or more of leads 18, 20 or 44 in conjunction with housing 52. In some embodiments, housing 52 includes two or more electrodes, and IMD 10 may detect electrical signals generated by heart 12 with the two or more electrodes disposed in housing 52.

Referring now to FIG. 2, an exemplary feedthrough 33 is shown. Conductors 22, 24, 34 and 36 conduct electrical signals from an upper portion 32' within connector block 32 to a lower portion that resides within housing 52. Conductors 22, 24, 34 and 36 are the conductors that electrically couple electrodes of the leads to IMD 10. For example, conductors 22 and 24 may be electrically connected to electrodes 22 and 24 of lead 18 and conductors 34 and 36 may be electrically connected to electrodes 34 and 36 of lead 20. Although only four conductors are illustrated as passing through feedthrough 33 for ease of illustration, the number of conductors that pass through feedthrough 33 typically depends on the number of electrodes and the number of leads of IMD 10 and may be more or less than four.

FIG. 3 illustrates the electrical equivalent of feedthrough 33. As can be seen, a capacitance 35 may be associated with each conductor extending through feedthrough 33. This may provide some form of filtering for the protection of the internal circuitry, however, given the strong fields generated during an MRI procedure, there exists a risk of damage to the internal circuitry or the creation of a false need to deliver therapy to the patient if the induced MRI energy is interpreted to be a sense signal. Accordingly, the present invention includes a stub filter 37 coupled to each conductor 22, 24, 34 and 36. The stub filter 37 can be placed inside the housing 52 as shown with conductors 22 and 24. Alternately, the stub filter 37 can reside in the connector block 32 as shown with conductors 34 and 36. According to the invention, the stub filter 37 has an electrical length of approximately one-quarter wavelength of the frequency of an MRI scanner or other interference source that one desires to provide protection from. Stub filter 37 is essentially an open circuit terminated transmission line, which causes a standing wave to be created by reflecting the incident energy back toward the connection point of each connector. Since the stub filter (transmission line) 37 is one-quarter wavelength of the frequency of an MRI RF signal the reflected wave is 180 degrees out of phase with the incident wave and the two signals add destructively and substantially cancel one another out. The resulting stub filter is highly frequency selective and operates to attenuate the signal having the frequency of the undesired interfering signal while allowing signals at all other frequencies or at least signals at desired frequencies to pass relatively unimpeded. This effectively prevents the induced energy of the interfering radiating signal (e.g., MRI RF signal) from reaching the internal circuitry of the IMD thereby protecting the device as well as the patient from having unnecessary therapy delivered.

Figure 4:
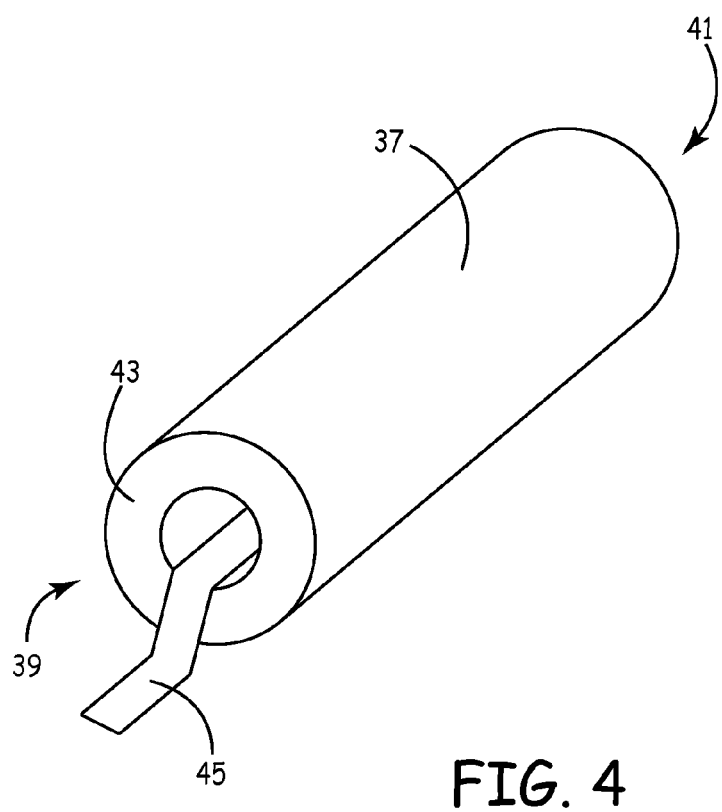
FIG. 4 is an illustration of a transmission line stub filter according to one embodiment.

Referring now to FIG. 4, an illustration of a one-quarter wavelength stub filter (or open circuit terminated transmission line) 37 is shown. Stub filter 37 is formed from a dielectric material 43 and a conductor 45.

The stub filter 37 is coupled at one end 39 to the respective conductor of one of the leads such as by soldering or other electrical connection technique. The other end 41 of stub filter 37 is an open circuit. Conductor 45 disposed within the stub filter 37 and has an electrical length approximately equal to one-quarter of the wavelength of the interfering radiating field, e.g., the RF of an MRI scanner. As such, the interfering radiating signal is sent down conductor 45 of stub filter 37. Upon reaching end 41 of the stub filter, the interfering radiating signal is reflected back down conductor 45 of stub filter 37 at near 100 percent efficiency. Upon arriving back at end 39, the reflected signal is now approximately 180 degrees out of phase of the original signal (since it is now one-half of a wavelength later). In other words, the reflected signal of the open circuit terminated transmission line is a phase-shifted version of the interfering signal. The reflected signal adds destructively to the incoming interfering signal, thereby greatly attenuating the interfering radiating signal.

According to one embodiment of the present invention, the stub filter 37 is comprised of a high dielectric material 43 so that the physical length of the stub filter is suitable for use in an implanted medical device or other small geometry applications. The dielectric constant required to obtain a particular physical size suitable for any application can be determined by the following equation:

$$\lambda = [1/sqrt(Ur*Er)]*C/F,$$

where $\lambda$ is the wavelength, F is the frequency to be attenuated or cancelled, C is the speed of light, Ur is relative permeability, and Er is the dielectric constant value. The frequency to be attenuated or cancelled (F) is 64 MHz for 1.5 Tesla MRI scanners and 128 MHz for 3 Tesla MRI scanners. In some examples, the dielectric constant may be a high dielectric constant, e.g., a dielectric constant greater than 9000.

For stub filter 37 to attenuate or cancel a 64 MHz MRI signal, and using a nonferromagnetic material (thus providing a Ur=1), $\lambda$ would equal 1.89 inches if an Er of 9500 was used. An Er of this magnitude is available, for example, in Z5V Barium Titanate. Accordingly, one-quarter wavelength (¼$\lambda$) would then be 0.4725 inches, which is a suitable length for use in an IMD unlike other techniques, such as shunting, where the physical length of the shunt would be too large for practical application in an IMD at MRI frequencies.

Figure 5:
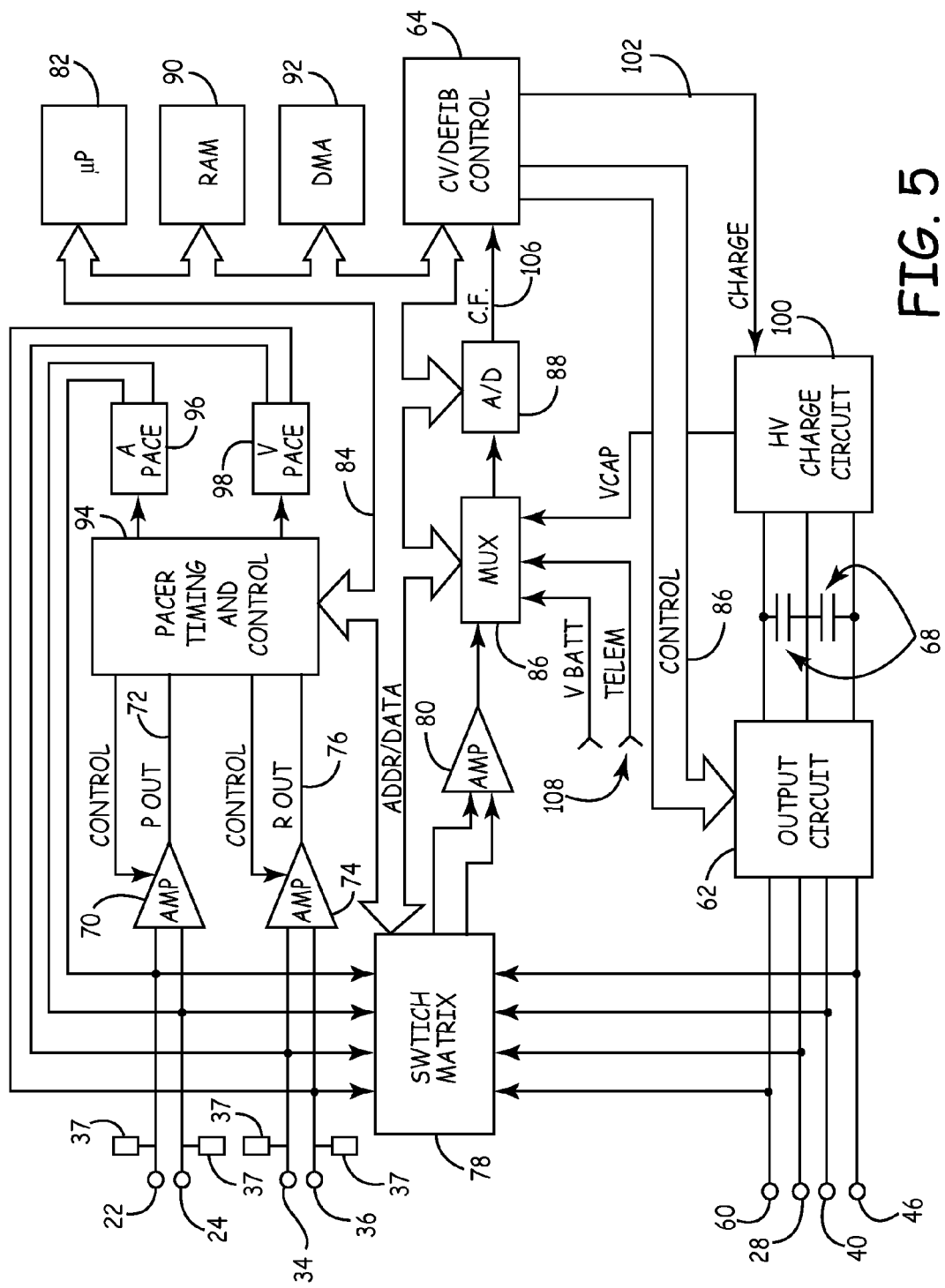
FIG. 5 is a block diagram of an IMD utilizing the techniques of this disclosure.

FIG. 5 is a functional schematic diagram of one embodiment of IMD 10 according to the present invention. FIG. 5 includes electrode terminals 22, 24, 28, 34, 36, 40 and 46, which correspond to the electrodes shown in FIG. 1. As can be seen one-quarter wavelength (at 64 MHz or 128 MHz for MRI RF frequencies) transmission lines (or stub filters) 37 are coupled to electrode terminals 22, 24 34 and 36. These transmission lines create a reflected signal that attenuates the incident wave from an MRI scanner (or other device generating an interfering radiating signal) from reaching the amplifiers 70 and 74, internal rectification circuits or other circuitry within IMD 10. In this way, incident MRI energy will not be interpreted to be valid cardiac sensed signals thereby protecting the patient from receiving unnecessary therapy. Moreover, the amplifiers and other circuitry are protected from any damaging energy that might otherwise impede the proper operation of the IMD.

Electrode 60 corresponds to the uninsulated portion of housing 52 of IMD 10. In some embodiments, housing 52 may include a second electrode (not shown). Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 may comprise an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold.

Electrodes 34 and 36, located in right ventricle 16, are coupled to an R-wave amplifier 74. Amplifier 74 may comprise an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74.

A switch matrix 78 selects electrodes for coupling to a wide band amplifier 80 for use in digital signal analysis. Selection of electrodes is controlled by microprocessor 82 via data/address bus 84. As shown in FIG. 5, microprocessor 82 can control switch matrix 78 to select any of pace/sense electrodes 22, 24, 34, 36, and any of defibrillation electrodes 28, 40, 46, and can electrode 60. In this way, microprocessor 82 controls which electrodes are selected as sensors to sense electrical signals from heart 12.

The signals from the selected electrodes are provided to multiplexer 86, and are thereafter converted to multi-bit digital signals by A/D converter 88. The signals may be stored in random access memory (RAM) 90 under control of direct memory access (DMA) circuit 92. Microprocessor 82 selects the electrodes used as sensors to sense cardiac electrical signals, further processes the signals to monitor one or more cardiac parameters.

Digital signal analysis includes, but is not limited to, analysis of the electrical signals sensed via the selected electrodes, and may include operations such as amplifying, rectifying, filtering, summing and integrating. Digital signal analysis also may include morphological analysis, such as analysis employing wavelet, Fourier or similar spectral analysis techniques.

In particular, digital signal analysis includes determination of at least one cardiac parameter. Microprocessor 82 measures the amplitude of the QRS complex, or the integral of the QRS complex, or the integral of the QRST segment. The QRS complex or QRST segment may be rectified prior to measurement. In a typical application, microprocessor 82 selects the signal sensed between can electrode 60 and a defibrillation coil electrode 28, 40 or 46, and evaluates the QRS complex or QRST segment of the signal sensed by the selected electrodes. Microprocessor 82 may also select the signal sensed between two can electrodes.

In typical conditions, IMD 10 uses signals sensed via electrodes 22, 24, 34 and 36 to determine whether to administer cardiac pacing, cardioversion or defibrillation therapies. Pacer timing/control circuitry 94 receives signals from P-out line 72 and R-out line 76, and computes various timing intervals as a function of the timing of the received signals. Pacer timing/control circuitry 94 also may include programmable digital counters that control pacing according to any of several pacing modes. Pacer output circuitry 96 and 98, which are coupled to electrodes 22, 24, 34 and 36, generate pacing stimuli under the control of pacer timing/control circuitry 94. The IPG of IMD 10 comprises microprocessor 82, in cooperation with pacer timing/control circuitry 94 and pacer output circuitry 96 and 98.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. An implantable medical device operable to sense signals from a patient or to provide a therapy to anatomical tissue of the patient in the presence of an interfering signal, comprising:
    a housing that includes circuitry;
    a connector block on the housing;
    at least one lead coupled at a proximal end to the implanted medical device and configured to be coupled at a distal end to the anatomical tissue, the at least one lead having a conductor therein that is configured to be electrically coupled to the circuitry within the implanted medical device; and
    an open circuit terminated transmission line having an electrical length approximately equal to one-quarter of a wavelength of the interfering signal, the open circuit terminated transmission line being electrically coupled to the conductor at the proximal end of the lead,
    wherein the interfering signal comprises a magnetic or electric field generated by a magnetic resonance imaging (MRI) scanner during an MRI scan,
    wherein the open circuit terminated transmission line resides within the connector block,
    wherein the open circuit terminated transmission line has a high dielectric constant, and
    wherein the open circuit terminated transmission line is configured to cause a phase-shifted version of the interfering signal to be reflected through the open circuit terminated transmission line to attenuate the interfering signal.

2. The device of claim 1, wherein the phase-shifted version comprises a signal approximately 180 degrees out of phase with the interfering signal.

3. The device of claim 1, wherein the high dielectric constant is greater than 9000.

4. The device of claim 1, wherein the interfering signal has a frequency of 64 MHz.

5. The device of claim 1, wherein the interfering signal has a frequency of 128 MHz.

6. A method for operating a medical device implanted in a patient undergoing a magnetic resonance imaging (MRI) procedure, comprising:
    providing at least one lead coupled at a proximal end to the implanted medical device and coupled at a distal end to the anatomical tissue, the at least one lead having a conductor therein that is electrically coupled to circuitry within the implanted medical device; and
    electrically coupling an open circuit terminated transmission line having an electrical length approximately equal to one-quarter wavelength of a signal generated by an MRI scanner during the MRI procedure to the conductor near the proximal end of the lead thereby causing a phase-shifted version of the signal to be reflected through the open circuit terminated transmission line to attenuate the signal generated by the MRI scanner during the MRI procedure.

7. The method of claim 6, wherein the open circuit terminated transmission line is a high dielectric open circuit terminated transmission line, and wherein electrically coupling the open circuit terminated transmission line to the conductor comprises electrically coupling the high dielectric open circuit terminated transmission line to the conductor.

8. The method of claim 7, wherein the high dielectric open circuit terminated transmission line is an open circuit terminated transmission line having a dielectric constant greater than 9000, and wherein electrically coupling the high dielectric open circuit terminated transmission line to the conductor comprises electrically coupling the open circuit terminated transmission line having the dielectric constant greater than 9000 to the conductor.

9. An implantable medical device operable to sense signals from a patient or to provide a therapy to anatomical tissue of the patient during a magnetic resonance imaging (MRI) procedure, comprising:
   at least one lead coupled at a proximal end to the implanted medical device and configured to be coupled at a distal end to the anatomical tissue, the at least one lead having a conductor therein that is configured to be electrically coupled to circuitry within the implanted medical device; and
   a high dielectric open circuit terminated transmission line having an electrical length approximately equal to one-quarter wavelength of a signal generated by an MRI scanner during the MRI procedure, the high dielectric open circuit transmission line being electrically coupled to the conductor near the proximal end of the lead,
   wherein, the high dielectric open circuit terminated transmission line is configured to cause an approximately 180 degree phase-shifted version of the signal to be reflected through the high dielectric open circuit terminated transmission line to attenuate the signal generated by the MRI scanner during the MRI procedure.

10. The device of claim 9, wherein the high dielectric open circuit terminated transmission line has a high dielectric constant that is greater than 9000.

11. The device of claim 9, wherein the high dielectric open circuit terminated transmission line resides inside a housing containing the circuitry.

12. The device of claim 9, wherein the high dielectric open circuit terminated transmission line resides within a connector block on a housing containing the circuitry.

13. The device of claim 9, wherein the high dielectric open circuit terminated transmission line comprises a high dielectric tube having an open circuit terminated transmission line positioned within the high dielectric tube.

14. The device of claim 13, wherein the high dielectric tube has a length less than one half inch.

15. The device of claim 9, wherein the interfering signal generated by the MRI scanner during the MRI procedure has a frequency of approximately one of 64 MHz or 128 MHz.

* * * * *